United States Patent [19]

Bundy

[11] 4,148,825

[45] Apr. 10, 1979

[54] 2-DECARBOXY-2-ALKYLCARBONYL-11-DEOXY-PGF COMPOUNDS

[75] Inventor: Gordon L. Bundy, Portage, Mich.

[73] Assignee: The Upjohn Company, Kalamazoo, Mich.

[21] Appl. No.: 925,261

[22] Filed: Jul. 17, 1978

Related U.S. Application Data

[62] Division of Ser. No. 888,695, Mar. 21, 1978, Pat. No. 4,123,463.

[51] Int. Cl.² .................................... C07C 177/00
[52] U.S. Cl. ............................ 260/586 R; 260/590 C
[58] Field of Search ...................... 260/586 R, 590 C

[56] References Cited

U.S. PATENT DOCUMENTS

| 3,931,296 | 1/1976 | Hayashi et al. ............... 560/121 |
| 3,953,435 | 4/1976 | Hayashi et al. ............... 542/426 |
| 4,066,751 | 1/1978 | Hayashi et al. ............... 560/121 |

OTHER PUBLICATIONS

Derwent CPI Farmdoc 93049x/50 (JA-044211).
Derwent Farmdoc CPI No. 35953x.
Derwent Farmdoc CPI No. 94924x.

*Primary Examiner*—Gerald A. Schwartz
*Attorney, Agent, or Firm*—Robert A. Armitage

[57] ABSTRACT

The present invention provides novel prostaglandin analogs wherein the C-2 carboxyl is replaced by alkylcarbonyl, i.e., a C-2 ketone. These novel 2-decarboxy-2-alkylcarbonyl-PG-type compounds are disclosed as improved gastrointestinal cytoprotective agents, being devoid or substantially devoid of other prostaglandin-type effects (e.g., smooth muscle or cardiovascular).

41 Claims, No Drawings

2-DECARBOXY-2-ALKYLCARBONYL-11-DEOXY-PGF COMPOUNDS

The present application is a divisional application of Ser. No. 888,695, filed Mar. 21, 1978, now U.S. Pat. No. 4,123,463.

The present invention relates to prostaglandin analogs, for which the essential material constituting disclosure therefor is incorporated by reference here from now U.S. Pat. No. 4,123,463.

I claim:

1. A prostaglandin analog of the formula

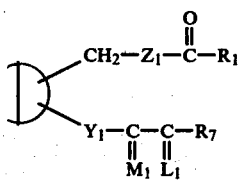

wherein ⌓ is

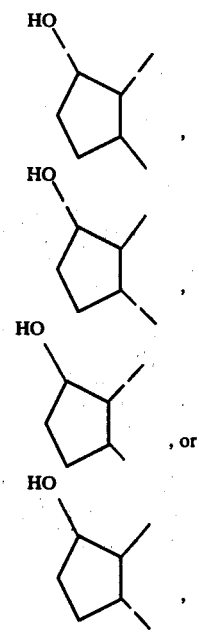

wherein $R_1$ is alkyl of one to 4 carbon atoms, inclusive; wherein $L_1$ is

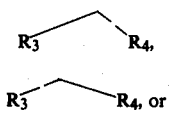

a mixture of

and

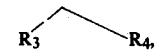

wherein $R_3$ and $R_4$ are hydrogen, methyl, or fluoro, being the same or different, with the proviso that one of $R_3$ and $R_4$ is methyl only when the other is hydrogen or methyl; wherein $M_1$ is

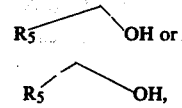

wherein $R_5$ is hydrogen or methyl; wherein $R_7$ is

 (1)

 (2)

 (3)

wherein h is zero to three, inclusive, wherein m is one to 5, inclusive, s is zero, one, 2, or 3 and T is chloro, fluoro, trifluoromethyl, alkyl of one to 3 carbon atoms or alkoxy of one to 3 carbon atoms, the various T's being the same or different, with the proviso that not more than two T's are other than alkyl; wherein $Y_1$ is
  (1) trans—CH=CH—
  (2) cis—CH=CH—
  (3) —CH$_2$CH$_2$—, or
  (4) —C≡C—; and
wherein $Z_1$ is
  (1) cis—CH=CH—CH$_2$—(CH$_2$)$_g$—CH$_2$—,
  (2) cis—CH=CH—CH$_2$—(CH$_2$)$_g$—CF$_2$—,
  (3) cis—CH$_2$—CH=CH—(CH$_2$)$_g$—CH$_2$—,
  (4) —(CH$_2$)$_3$—(CH$_2$)$_g$—CH$_2$—,
  (5) —(CH$_2$)$_3$—(CH$_2$)$_g$—CF$_2$—,
  (6) —CH$_2$—O—CH$_2$—(CH$_2$)$_g$—CH$_2$—,
  (7) —(CH$_2$)$_2$—O—(CH$_2$)$_g$—CH$_2$—,
  (8) —(CH$_2$)$_3$—O—(CH$_2$)$_g$—,
  (9) —C≡C—CH$_2$—(CH$_2$)$_g$—CH$_2$—,
  (10) —CH$_2$—C≡C—(CH$_2$)$_g$—CH$_2$—, or
  (11) trans—(CH$_2$)$_2$—(CH$_2$)$_g$—CH=CH—, wherein g is one, two, or three.

2. A prostaglandin analog according to claim 1, wherein $R_1$ is methyl.

3. A prostaglandin analog according to claim 2, wherein ⌓ is

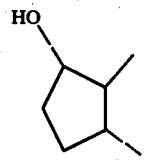

4. 2-Decarboxy-2-methylcarbonyl-11-deoxy-8β, 12α-PGF$_2$α, a prostaglandin analog according to claim 3.

5. A prostaglandin analog according to claim 2, wherein ⌓ is

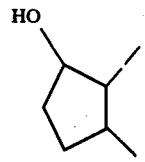

6. 2-Decarboxy-2-methylcarbonyl-11-deoxy-PGF$_2\beta$, a prostaglandin analog according to claim 5.

7. A prostaglandin analog according to claim 2, wherein p is

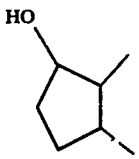

8. 2-Decarboxy-2-methylcarbonyl-11-deoxy-8$\beta$, 12$\alpha$-PGF$_2\beta$, a prostaglandin analog according to claim 7.

9. A prostaglandin analog according to claim 2, wherein p is

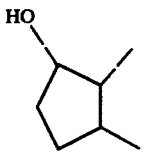

10. A prostaglandin analog according to claim 9, wherein Y$_1$ is cis—CH=CH—.

11. 2-Decarboxy-2-methylcarbonyl-13-cis-11-deoxy-PGF$_2\alpha$, a prostaglandin analog according to claim 10.

12. A prostaglandin analog according to claim 9, wherein Y$_1$ is —CH$_2$—CH$_2$—.

13. 2-Decarboxy-2-methylcarbonyl-13,14-dihydro-11-deoxy-PGF$_2\alpha$, a prostaglandin analog according to claim 12.

14. A prostaglandin analog according to claim 9, wherein Y$_1$ is —C≡C—.

15. 2-Decarboxy-2-methylcarbonyl-13,14-didehydro-11-deoxy-PGF$_2\alpha$, a prostaglandin analog according to claim 14.

16. A prostaglandin analog according to claim 9, wherein Y$_1$ is trans—CH=CH—.

17. A prostaglandin analog according to claim 16, wherein R$_7$ is

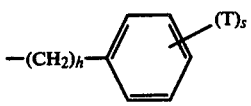

18. 2-Decarboxy-2-methylcarbonyl-17-phenyl-18,19,20-trinor-11-deoxy-PGF$_2\alpha$ a prostaglandin analog according to claim 17.

19. A prostaglandin analog according to claim 16, wherein R$_7$ is

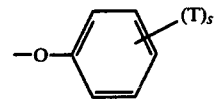

20. 2-Decarboxy-2-methylcarbonyl-16-phenoxy-17,18,19,20-tetranor-11-deoxy-PGF$_2\alpha$, a prostaglandin analog according to claim 19.

21. A prostaglandin analog according to claim 16, wherein R$_7$ is —(CH$_2$)$_m$—CH$_3$—.

22. A prostaglandin analog according to claim 21, wherein Z$_1$ is cis—CH=CH—CH$_2$—(CH$_2$)$_g$—CF$_2$—.

23. 2-Decarboxy-2-methylcarbonyl-2,2-difluoro-11-deoxy-PGF$_2\alpha$, a prostaglandin analog according to claim 22.

24. A prostaglandin analog according to claim 21, wherein Z$_1$ is cis—CH$_2$—CH=CH—(CH$_2$)$_g$—CH$_2$—.

25. 2-Decarboxy-2-methylcarbonyl-cis-4,5-didehydro-16,16-dimethyl-11-deoxy-PGF$_1\alpha$, a prostaglandin analog according to claim 24.

26. A prostaglandin analog according to claim 21, wherein Z$_1$ is (CH$_2$)$_3$—(CH$_2$)$_g$—CH$_2$—.

27. 2-Decarboxy-2-methylcarbonyl-11-deoxy-PGF$_1\alpha$, a prostaglandin analog according to claim 26.

28. A prostaglandin analog according to claim 21, wherein Z$_1$ is —(CH$_2$(3—(CH$_2$)$_g$—CF$_2$—.

29. 2-Decarboxy-2-methylcarbonyl-2,2-difluoro-11-deoxy-PGF$_1\alpha$, a prostaglandin analog according to claim 28.

30. A prostaglandin analog according to claim 21, wherein Z$_1$ is —CH$_2$—O—CH$_2$—(CH$_2$)$_g$—CH$_2$—.

31. 2-Decarboxy-2-methylcarbonyl-5-oxa-PGF$_1\alpha$, a prostaglandin analog according to claim 30.

32. A prostaglandin analog according to claim 21, wherein Z$_1$ is cis—CH=CH—CH$_2$—(CH$_2$)$_g$—CH$_2$—.

33. A prostaglandin analog according to claim 32, wherein R$_5$ is methyl.

34. 2-Decarboxy-2-methylcarbonyl-15-methyl-11-deoxy-PGF$_2\alpha$, a prostaglandin analog according to claim 32.

35. A prostaglandin analog according to claim 32, wherein R$_5$ is hydrogen.

36. A prostaglandin analog according to claim 35, wherein one of R$_3$ and R$_4$ is fluoro.

37. 2-Decarboxy-2-methylcarbonyl-16,16-difluoro-11-deoxy-PGF$_2\alpha$, a prostaglandin analog according to claim 36.

38. A prostaglandin analog according to claim 35, wherein at least one of R$_3$ and R$_4$ is methyl.

39. 2-Decarboxy-2-methylcarbonyl-16,16-dimethyl-11-deoxy-PGF$_2\alpha$, a prostaglandin analog according to claim 38.

40. A prostaglandin analog according to claim 35, wherein R$_3$ and R$_4$ are both hydrogen.

41. 2-Decarboxy-2-methylcarbonyl-11-deoxy-PGF$_2\alpha$, a prostaglandin analog according to claim 40.

* * * * *

UNITED STATES PATENT OFFICE
CERTIFICATE OF CORRECTION

Patent No. 4,148,825    Dated April 10, 1979

Inventor(s) Gordon L. Bundy

It is certified that error appears in the above-identified patent and that said Letters Patent are hereby corrected as shown below:

Column 2, lines 12-15,

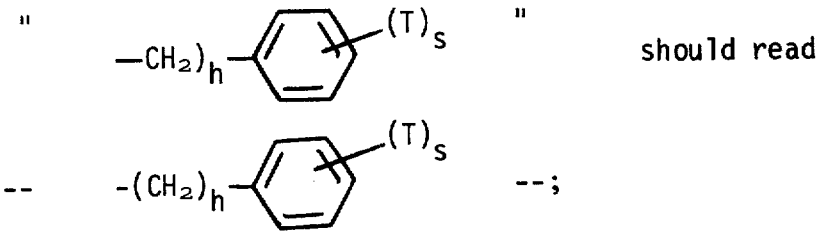

" ... " should read

-- ... --;

Column 3, line 32, "$Y_1$ is $-CH_2-CH_2-$." should read -- $Y_1$ is $-CH_2CH_2-$. --
Column 4, line 27, "$-(CH_2(_3-$" should read -- $-(CH_2)_3-$ --.

Signed and Sealed this

Fourth Day of September 1979

[SEAL]

Attest:

Attesting Officer

LUTRELLE F. PARKER
Acting Commissioner of Patents and Trademarks